(12) United States Patent
Wombacher et al.

(10) Patent No.: US 7,686,884 B2
(45) Date of Patent: Mar. 30, 2010

(54) USE OF PHOSPHORUS-OXYGEN ACID ESTERS CONTAINING ALKOXY GROUPS AS CORROSION INHIBITORS FOR REINFORCED CONCRETE

(75) Inventors: Franz Wombacher, Oberlunkhofen (CH); Beat Marazzani, Oberengstringen (CH); Urs Mäder, Frauenfeld (CH)

(73) Assignee: Sika Technology AG, Baar (CH)

( * ) Notice: Subject to any disclaimer, the term of this patent is extended or adjusted under 35 U.S.C. 154(b) by 1121 days.

(21) Appl. No.: 10/555,280

(22) PCT Filed: May 4, 2004

(86) PCT No.: PCT/EP2004/050699

§ 371 (c)(1),
(2), (4) Date: Dec. 6, 2005

(87) PCT Pub. No.: WO2004/099098

PCT Pub. Date: Nov. 18, 2004

(65) Prior Publication Data

US 2006/0156960 A1    Jul. 20, 2006

(30) Foreign Application Priority Data

May 5, 2003    (EP) .................................. 03010130

(51) Int. Cl.
    *C04B 24/12*    (2006.01)
(52) U.S. Cl. ...................... 106/727; 106/14.05; 106/823
(58) Field of Classification Search ............... 106/14.05, 106/727, 823
    See application file for complete search history.

(56) References Cited

U.S. PATENT DOCUMENTS 2,574,516 A * 11/1951 Hornstein et al. ........... 558/177

4,120,655 A   10/1978  Crambes et al.
5,071,579 A   12/1991  Johnston

FOREIGN PATENT DOCUMENTS

| DE | 36 29 234 C1   | 10/1987 |
| GB | 2 248 612 A    | 4/1992  |
| JP | A-03-159945    | 7/1991  |
| WO | WO 88/01609 A1 | 3/1988  |

OTHER PUBLICATIONS

Answer 37 of 37 of STN Chem Abstracts Search: US 2,574,516 Walter (Nov. 13, 1951) abstract-.*
Answer 33 of 37 of STN Chem Abstracts Search DE 1099257 (also equiv to GB 895628) Blum et al., Motor Fuel Additives, Feb. 9, 1961, abstract.*
Answer 11 of 37 of STN Chem Abstracts Search DE 3530358 (Feb. 26, 1987) Von Bonin et al. abstract only.*
Answer 13 of 37 of STN Chem Abstracts Search: "Study of the mechanism of hydrogen sulfide corrosion and devlpmt of inhibitors for gas and petroleum industry", Rosenfeld et al., Rasrab Mer Zashch Met Korros Meshdunar Nauchno Tekh Kunf PRob SEV 3rd (1980), vol. 5, p. 75-81. Abstract Only.*
Mike Hayes et al.; "Use of migratory corrosion inhibitors"; *Construction Repair;* Jul./Aug. 1997; pp. 10-15.

* cited by examiner

*Primary Examiner*—Paul Marcantoni
(74) *Attorney, Agent, or Firm*—Oliff & Berridge, PLC

(57) ABSTRACT

Disclosed is a hydraulically setting composition containing phosphorus-oxygen acid esters or ester salts which comprise alkoxy groups. Also disclosed is a surface-modifying agent for structural steel, which contains or consists of phosphorus-oxygen acid esters or ester salts comprising alkoxy groups. The hydraulically setting composition and the surface-modifying agent are suitable for protecting reinforced concrete.

20 Claims, No Drawings

USE OF PHOSPHORUS-OXYGEN ACID ESTERS CONTAINING ALKOXY GROUPS AS CORROSION INHIBITORS FOR REINFORCED CONCRETE

FIELD OF THE INVENTION

The invention relates to the corrosion inhibition of reinforced concrete. In particular, it relates to hydraulically setting compositions and surface-modifying agents for structural steel.

DESCRIPTION OF THE PRIOR ART

Steel as a reinforcing material in structures is widely used. Of particular importance is reinforcing steel. The steel is placed in a hydraulically setting material and reinforces the latter. Of particular importance is reinforced concrete. The corrosion of steel, which is present in hydraulically set materials, is of very great economic interest. As a result of the corrosion of the steel reinforcement, the strength thereof and hence the strength of the concrete are reduced. In addition, the corrosion products, such as, for example, iron oxides or hydrated iron oxides, have a larger volume than the uncorroded steel itself. This results in stresses in the concrete which may lead to cracks or to chipping off of whole pieces.

The corrosion of the steel present in the concrete is a substantially diffusion-controlled process. Water and oxygen can diffuse into the pores of the concrete. Pore water contains, inter alia, dissolved $Ca(OH)_2$ and, in intact concrete, has a pH of about 13. At this pH, steel reinforcements embedded in concrete are protected from corrosion by a passivation layer. The diffusion of atmospheric $CO_2$ into the pores results, inter alia, in the formation of insoluble $CaCO_3$, and the pH of the pore water decreases to values of less than 9. At these pH values, however, the passivation layer on the steel loses its effect. The effect of the passivation layer can also be impaired or eliminated by chloride ions. Chloride ions can penetrate into the concrete, for example, by contact of the concrete with sea water or deicing agents. The amount of $CO_2$ or chloride penetrating is smaller with the use of particularly dense, low-pore concrete. However, the penetration also cannot be completely prevented in this manner. Moreover, on changing the structure of the concrete, the properties thereof also change, which is frequently undesired depending on the intended use. The possibility of using low-pore concrete is therefore not viable in many cases.

It is known that corrosion inhibitors, such as, for example, nitrites, amines, alkanolamines, mixtures thereof with inorganic or organic acids or phosphoric acid esters, can be added to fresh concrete. It is also known that phosphonic acids or phosphonic acid derivatives can be used for corrosion inhibition in concrete. DE-A 36 29 234 discloses the addition of salts, in particular Na salts of various alkylphosphonic acids, as an additive to concrete mixes and mortar mixes. GB-A 2 248 612 and JP-A 03-159945 disclose phosphonic acids containing amino or hydroxyl groups as an additive to concrete.

Compounds containing phosphonic acid groups, such as aminotrismethylenephosphonic acid or 2-phosphonobutane-1,2,4-tricarboxylic acid, are known corrosion inhibitors for steel. However, these substances retard the hardening of hydraulically setting binders. For corrosion inhibition of reinforced concrete, doses in the range of about 0.2 to 1.5 percent by mass (based on the cement mass) would be required in the case of such phosphonic acid compounds. However, such a high dose leads to a considerable reductions of the early strength values of the cement-based products produced therewith and is therefore often undesired.

In addition to the corrosion-inhibiting treatment of fresh concrete, the question of protecting steel reinforcement in old concrete frequently arises in practice, particularly in the case of renovations. For this purpose, the concrete can be superficially removed or blasted off and the steel reinforcement exposed. After removal of corrosion products by, for example, sandblasting, the steel reinforcement can then be treated with corrosion inhibitors or products containing corrosion inhibitors and finally covered again or reprofiled with concrete or a repair mortar. This method is used especially in cases of advanced corrosion of the reinforcing steel (where the cross-sectional loss is too great, this should be replaced by new reinforcing steel) and chipping of concrete, and in the presence of relatively high chloride concentrations in the concrete layer covering the steel reinforcement.

It is furthermore known that the surface of hardened reinforced concrete can be treated with a penetrating corrosion inhibitor. This technique is disclosed, for example, in "M. Haynes, B. Malric, *Construction Repair*, July/August 1997" or in U.S. Pat. No. 5,071,579. For this purpose, a solution of the corrosion inhibitor is applied or sprayed several times in succession onto the concrete surface, the corrosion inhibitor penetrating the surface. The further penetration into the interior down to the steel reinforcement is usually promoted by the repeated application of water to the surface. It is known that $Na_2PO_3F$ can be used as a penetrating corrosion inhibitor. U.S. Pat. No. 5,071,579 also discloses the combined use of $Na_2PO_3F$ together with a phosphonic acid of the formula $R_nR_lN(CH_2PO_3H_2)_{2-n}$ (n=0 or 1).

However, this technique has a number of advantages. In order to be able to display their effect, the corrosion inhibitors must penetrate through the concrete to the steel reinforcement. Depending on the thickness of the concrete covering, a distance of several centimeters may be involved and the penetration takes a correspondingly long time. Sodium fluorophosphate is moreover hydrolyzed in a strongly alkaline medium and, with $Ca(OH)_2$ dissolved in the pore water, forms sparingly soluble (in the unhydrolyzed state: only moderately soluble) calcium salts which can penetrate into the concrete only with difficulty. Phosphonic acids too can form sparingly soluble calcium salts. A considerable part of the applied amount of these corrosion inhibitors thus does not reach the steel reinforcement at all and accordingly also cannot display a corrosion-inhibiting effect. The inhibitors must therefore be used in large amounts. This is uneconomical and moreover the concrete is loaded with undesired components thereby.

SUMMARY OF THE INVENTION

It was therefore an object of the present invention to provide hydraulically setting compositions as well as surface-modifying agents for structural steel which contain or consist of readily penetrating, highly effective corrosion inhibitors for steel which form no insoluble or sparingly soluble calcium salts.

Surprisingly, it was found that hydraulically setting compositions as claimed in claim 1 and surface-modifying agents for structural steel as claimed in claim 8 achieve the object.

It was surprisingly found that the 'alkoxy corrosion inhibitors' have an excellent corrosion-inhibiting effect with respect to reinforcing steel or structural steel, but without having a substantial influence on the hardening behavior and the processing properties of cement-based mortars and concrete.

DESCRIPTION OF THE PREFERRED EMBODIMENTS

The present invention relates firstly to a hydraulically setting composition which contains esters or ester salts, comprising alkoxy groups, of phosphorus-oxygen acids of the general formula (I), (II), (III) or (IV)

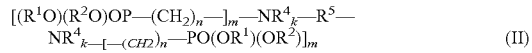

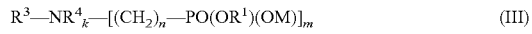

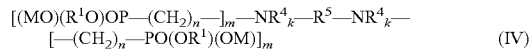

where
n is an integer from 0 to 10,
m+k is 2 and m is 1 or 2 and k is 0 or 1,
at least one of the radicals $R^1$, $R^2$ and optionally $R^3$ is an alkoxy group of the general formula —[$CH_2$—$CHR^6$—O]$_l$$R^7$, where l is from 2 to 30 and $R^6$ and $R^7$ are each H or $CH_3$,
and the radicals $R^1$ and $R^2$, where they are not alkoxy groups, are straight-chain or branched, optionally substituted $C_1$- to $C_6$-alkyl groups,
and $R^3$, where it is not an alkoxy group, is a straight-chain or branched, optionally substituted, $C_1$- to $C_{20}$-alkyl group or aryl group,
$R^4$ is H or a straight-chain or branched, optionally substituted $C_1$- to $C_6$-alkyl group,
$R^5$ is a divalent, bridging group, and
M is at least one cation selected from the group consisting of alkali metal, alkaline earth metal or ammonium ions.

Here and below, the expression "alkoxy corrosion inhibitors" designates esters or ester salts of phosphorus-oxygen acids of the general formula (I), (II), (III) or (IV), which esters or ester salts comprise alkoxy groups described above.

The formulae of the 'alkoxy corrosion inhibitors' (I) to (IV) show that the phosphorus is present directly on the nitrogen atom (n=0) or is separated therefrom by an alkylene group n>0). The alkylene group is described by the index n, where n is an integer between 1 and 10, in particular between 1 and 3. Preferably n is 1 or 0, particularly preferably n is 1.

The index m is 1 or 2 and the index k is 0 or 1, the sum of m+k being 2. Preferably, m and k are each 1, i.e. in each case only one —($CH_2$)$_n$—PO(O$R^1$)(O$R^2$) group or —($CH_2$)$_n$—PO(O$R^1$)(OM) group is directly linked to a nitrogen atom.

At least one of the radicals $R^1$, $R^2$ and optionally (i.e. where the compounds of the formula (I) or (III) are present) $R^3$ is an alkoxy group. Suitable alkoxy groups are in particular polyoxyethylene or polyoxypropylene groups of the general formula —[$CH_2$—$CHR^6$—O]$_l$$R^7$, where l is from 2 to 30 and $R^6$ is H and/or $CH_3$. $R^6$ is preferably H, i.e. the alkoxy group is a polyoxyethylene group. l is preferably from 3 to 20 and particularly preferably from 5 to 15. $R^7$ is a CH group or H.

It is known to the person skilled in the art that such alkoxy groups are obtainable, for example, by oxyalkylation or starting from industrial polyglycols. Said values for l are therefore average chain lengths, where the average value need not of course be a natural number but can also be any desired rational number.

The radicals $R^1$ and $R^2$, where they are not alkoxy groups, are straight-chain or branched, optionally substituted $C_1$- to $C_6$-alkyl groups. By way of example, here they are a methyl, ethyl, n-propyl, isopropyl, n-butyl, n-pentyl or hexyl group. They are preferably a methyl or ethyl group and very particularly preferably an ethyl group. A substituted alkyl group may be in particular a 2-methoxyethyl group.

The radical $R^3$, where it is not an alkoxy group, is a straight-chain or branched, optionally substituted, $C_1$- to $C_{20}$-alkyl group or aryl group. $C_1$- to $C_{20}$-alkyl groups are preferred. Examples of suitable groups include, methyl, ethyl, n-propyl, isopropyl, n-butyl, isobutyl, n-pentyl, n-hexyl, 2-ethylhexyl, n-heptyl, n-octyl, n-nonyl, n-decyl or n-dodecyl groups. Particularly preferred groups are n-propyl, n-butyl, n-octyl and 2-ethylhexyl groups. A substituted alkyl group may be in particular a ω-methoxyalkyl group, e.g. methoxyethyl group. Aryl groups may be pure aryl groups, such as alkyl-substituted aryl groups, for example a —$CH_2C_5H_6$ group.

The radical $R^4$, if present, is a H or a straight-chain or branched, optionally substituted $C_1$- to $C_6$-alkyl group. Particularly preferably, $R^4$ is H or methyl. A substituted alkyl group may be in particular a 2-methoxyethyl group.

In the bridged compounds of the formulae (II) and (IV), no $R^3$ is present but instead a divalent, bridging group $R^5$, which preferably has at least 2 carbon atoms. Said groups may be in particular groups derived from aliphatic, alicyclic or aromatic hydrocarbons. The examples include 1,4-xylylene, 1,4-cyclohexylylene or ethylidene groups which may optionally also have hetero atoms or substituents. The bridging group is preferably an alkylene group having 2 to 20 carbon atoms, in which nonneighboring $CH_2$ groups may also be substituted by O or N atoms. Examples include —($CH_2$)$_2$—, —($CH_2$)$_4$—, —($CH_2$)$_6$—, —($CH_2$)$_8$—, —($CH_2$)$_2$—O—($CH_2$)$_2$—, —($CH_2$)$_2$—O—($CH_2$)$_2$—O—($CH_2$)$_2$—, —($CH_2$)$_3$—O—($CH_2$)$_2$—O—($CH_2$)$_2$—O—($CH_2$)$_3$—, —($CH_2$)$_2$—O—($CH_2$)$_2$—O—($CH_2$)$_2$—O—($CH_2$)$_2$—O—($CH_2$)$_2$—, —($CH_2$)$_3$—O—($CH_2$)$_4$—O—($CH_2$)$_3$—, —($CH_2$)$_2$—O—[($CH_2$)$_2$—O—]$_j$($CH_2$)$_2$—O—($CH_2$)$_2$—, —($CH_2$)$_2$—HN—($CH_2$)$_2$ or —($CH_2$)$_2$—$NR_6$—($CH_2$)$_2$—$NR_6$—($CH_2$)$_2$ groups, where j is a number from 1 to 10 and $R_6$ corresponds to alkyl, —($CH_2$)$_n$—PO(O$R^1$)(O$R^2$) or —($CH_2$)$_n$—PO(O$R^1$)(OM). $R^5$ is preferably —($CH_2$)$_2$—($CH_2$)$_4$—, —($CH_2$)$_6$—, —($CH_2$)$_3$—O—($CH_2$)$_4$—O—($CH_2$)$_3$—, —($CH_2$)$_2$—O—($CH_2$)$_2$—O—($CH_2$)$_2$ or —($CH_2$)$_2$—O—($CH_2$)$_2$—O—($CH_2$)$_2$—O—($CH_2$)$_2$ groups.

The compounds of the formulae (I) and (II) are esters of phosphorus-oxygen acids, while the compounds of the formulae (III) and (IV) are ester salts of phosphorus-oxygen acids. These ester salts have one ester group per phosphorus atom. The radicals should be chosen as above. In the case of formula (IV), $R^1$ is in every case an alkoxy group.

The ester salts have —($CH_2$)$_n$—PO(O$R^1$)(OM) groups. M is at least one cation selected from the group consisting of alkali metal, alkaline earth metal or ammonium ions. The ammonium ions may be $NH_4^+$, (HOCH$_2$CH$_2$)$_3$NH$^+$, (HOCH$_2$CH$_2$)$_2$NH$_2^+$, HOCH$_2$CH$_2$NH$_3^+$, HOCH$_2$CH$_2$N(CH$_3$)H$_2^+$, (HOCH$_2$CH$_2$)$_2$N(CH$_3$)H$^+$ or HOCH$_2$CH$_2$N(CH$_3$)$_2$H$^+$, it may also be tetraalkylammonium ions, such as, for example, tetramethylammonium or tetraethylammonium. Na$^+$, K$^+$, Mg$^{++}$, Ca$^{++}$, Ce$^{+++}$, Al$^{+++}$, Zn$^{++}$ or NH$_4^+$ are preferred. For the sake of simplicity, the above formulae represent only the case of monovalent cations. However, the person skilled in the art can easily derive the correct formulae for polyvalent cations therefrom.

Among the various possible combinations for the radicals $R^1$ to $R^7$ and M, the person skilled in the art makes a suitable choice according to the desired properties and the intended use.

The preparation of the "alkoxy corrosion inhibitors" can be effected as follows:

The diesters of the phosphorus-oxygen acids can be prepared, for example, starting from commercially available phosphonic acid esters, such as, for example, diethyl phosphonate.

The term "diesters" is intended below to relate to the number of ester groups per phosphorus atom and hence to designate compounds in which all P atoms present in the molecule have in each case two ester groups. Correspondingly, the term "monoesters" is intended below to designate compounds in which each phosphorus atom has an ester group and a —OH or —O⁻ group.

An alkoxylated diester can be obtained therefrom by transesterification, by reacting diethyl phosphonate with the respective desired polyethylene or polypropylene glycol or the respective monoethers. The transesterification can be catalyzed, for example, by alkali metals, and liberated ethanol is distilled off.

It is of course also possible to start from phosphonic acid itself and to oxyalkylate it by the method known in principle to the person skilled in the art. In this case, alkoxy groups which still have a terminal OH group are obtained.

For n=0, the dialkoxyesters obtained can be reacted with the desired amine, such as, for example, ethylhexylamine. The reaction can be carried out in a manner known in principle in $CCl_4$ and a tertiary amine as a catalyst. The use of diamines, such as ethylenediamine, results in the formation of bridged diesters according to formula (II). The use of aminopolyethylene or polypropylene glycol results in the formation of diesters which have an alkoxy group as $R^3$.

Diesters having n=1 can be obtained by aminomethylation from the diethyl phosphonate or corresponding alkoxylated diester. Here, the phosphonic acid diester is reacted with formaldehyde, with the desired amine and with a suitable Brønsted acid.

Diesters having n=2 can be prepared by an addition reaction of amines with vinylphosphonic esters, and for n>2 by a free radical addition reaction of phosphonic acid diesters at double bonds (for example with allylamines for n=3) or the Arbuzov reaction with aminoalkyl bromides.

The ester salts are preferably prepared by alkaline hydrolysis of the diesters, for example by heating the diesters in aqueous NaOH to temperatures of from 60 to 100° C. for from 2 to 12 hours, substantially only one ester group per phosphorus atom being hydrolyzed. The optimum conditions for the respective desired compound can, if required, be determined by the person skilled in the art by means of only a few experiments. The ester salts also form in the hydrolysis of the diesters in concrete, it also being possible here for other cations to occur as opposite ions, depending on the type of concrete.

Hydraulically setting components of the hydraulically setting composition are those inorganic substances which harden under the influence of water. Examples of such hydraulically setting inorganic substances are, for example, cements, in particular cements according to European standard EN 197, in pure form or as a mixture with latently hydraulic binders, such as fly ash, blast furnace slag, oil shale slag, natural pozzolana or silicafume.

The hydraulically setting composition according to the invention may comprise further components, such as additives and auxiliaries, depending on the use.

Suitable additives are in particular inert fillers, in particular sand, gravel, stones and stone dust.

Auxiliaries which may be used are in particular hardening and/or setting accelerators, hardening and/or setting retarders, concrete plasticizers, corrosion inhibitors, water repellents or concrete waterproofers, air-entraining agents, thixotropic agents, anti foming agents, dyes, surfactants, odorous substances or biocides.

In an embodiment the hydraulically setting composition contains at least one corrosion inhibitor in addition to at least one 'alkoxy corrosion inhibitor'. Preferred corrosion inhibitors are aminoalcohols. These aminoalcohols may also be used as aminoalcohol salts, optionally as a mixture with aminoalcohols. Such aminoalcohol salts are preferably readily water-soluble. Suitable aminoalcohol salts are in particular the salts of aminoalcohols and organic acids, in particular of the $C_1$-$C_4$-carboxylic acids, $C_1$-$C_4$-hydroxycarboxylic acids or $C_2$-$C_4$-dicarboxylic acids. Corrosion inhibitors selected from the group consisting of monoethanolamine, diethanolamine, triethanolamine, N-methylethanolamine, N,N-dimethylethanolamine, N-ethylethanolamine, N,N-diethylethanolamine, N-methyldiethanolamine and 2-hydroxyethylethylenediamine and salts of organic acids thereof are particularly suitable.

A special case of the hydraulically setting compositions, after mixing these with water, constitutes the so-called cement slurries. These slurries substantially comprise a cement-water mixture and at least one 'alkoxy corrosion inhibitor'. Like the surface-modifying agents according to the invention, they are suitable as treatment agents for reinforcing steel, in particular for the use thereof, in the erection of a reinforcing concrete structure, and also as treatment agents for exposed reinforcing steel, in particular that in old concrete.

The hydraulically setting composition is prepared by mixing the components. In particular, the 'alkoxy corrosion inhibitors' are added to the dry binder, mortar or concrete or to the binder, mortar or concrete mixed with water, in the factory, on the building site, in the mixer, in the delivery pump or are added directly to the mix via a static mixer having a powder metering device or liquid metering device.

Secondly, the present invention relates to the surface-modifying agent for structural steel, which contains or consists of 'alkoxy corrosion inhibitors' as already defined.

The 'alkoxy corrosion inhibitors' can be used directly as surface-modifying agents for structural steel.

The surface-modifying agent according to the invention for structural steel may comprise further components, such as water, organic solvents, additives, such as antifoams, dyes, surfactants, emulsifiers, corrosion inhibitors, stabilizers, thickeners, odorous substances or biocides, depending on the use. It may be present in liquid form or, when suitable auxiliaries are added, may have a pasty or creamy consistency, which permits application of a larger amount per application step.

In an embodiment, the surface-modifying agent contains at least one corrosion inhibitor in addition to at least one 'alkoxy corrosion inhibitor'. Preferred corrosion inhibitors are aminoalcohols. These aminoalcohols may also be used as aminoalcohol salts, optionally as a mixture with aminoalcohols. Such aminoalcohol salts are preferably readily water-soluble. Suitable aminoalcohol salts are in particular the salts of aminoalcohols and organic acids, in particular of the $C_1$-$C_4$-carboxylic acids, $C_1$-$C_4$-hydroxycarboxylic acids or $C_2$-$C_4$-dicarboxylic acids. Corrosion inhibitors selected from the group consisting of monoethanolamine, diethanolamine, triethanolamine, N-methylethanolamine, N,N-dimethylethanolamine, N-ethylethanolamine, N,N-diethylethanolamine, N-methyldiethanolamine and 2-hydroxyethylethylenediamine and salts of organic acids thereof are particularly preferred.

Suitable thickeners are in particular thixotropic agents based on organic substances, such as castor oil derivatives, special polyamides, polyureas and polyurethanes, or those based on inorganic substances, such as chalks, kieselguhrs, pyrogenic silicas and bentonites, and organic carrier materials, for example silane-based ones.

Furthermore, combinations with other surface-modifying agents, such as, for example, water repellents in liquid or pasty consistency, are possible.

Water and organic solvents are suitable as solvents used. The choice is made from technical points of view, but preferably also from ecological points of view, such as, for example, human toxicity, water hazard classes or biodegradability.

Particularly suitable organic solvents are alcohols, preferably methanol, ethanol, propanol, isopropanol, higher alcohols, such as ethylene glycol, glycerol, polyetherpolyols, such as polyethylene glycols, and ether alcohols, such as butylglycol, methoxypropanol and alkylpolyethylene glycols.

Water is particularly preferred as the solvent. Furthermore, mixtures of water with alcohols having a water content of more than 50% by weight, preferably more than 65% by weight, in particular more than 80% by weight, are particularly preferred.

Depending on formulation and intended use of the surface-modifying agents, the solvents should be chosen so that the 'alkoxy corrosion inhibitor' or 'alkoxy corrosion inhibitors' used is or are soluble, partly soluble or insoluble in the solvent or solvent mixture. Partly soluble, or in particular insoluble solvents for 'alkoxy corrosion inhibitors' are preferably used when the surface-modifying agent is to be used in the form of emulsions or microemulsions or if an increase in the penetration behavior can be achieved therewith.

The surface-modifying agent for structural steel is preferably an aqueous or a substantially water-based solution of at least one 'alkoxy corrosion inhibitor' which particularly preferably has a pH between 7 and 13.

The concentration of the sum of all 'alkoxy corrosion inhibitors' used in the surface-modifying agent is chosen by the person skilled in the art according to the use and requirements. Typically, the proportion of the sum of all 'alkoxy corrosion inhibitors' in the surface-modifying agent is between 100 and 5% by weight, in particular between 100 and 10% by weight. A concentration range very suitable for customary applications for the sum of all 'alkoxy corrosion inhibitors' in the surface-modifying agent used is between 80 and 10% by weight, in particular between 50 and 10% by weight.

If additional components are present in the surface-modifying agent, these are mixed with the 'alkoxy corrosion inhibitors'. Depending on the type and consistency of the surface-modifying agent, the sequence in the admixing process may be of importance. It is also possible to prepare the surface-modifying agent in the form of a concentrate.

After preparation, the surface-modifying agent can be used directly or it can be modified again immediately before application. A particularly important modification is dilution with a solvent, in particular water.

The hydraulically setting composition according to the invention and the surface-modifying agent according to the invention are used for protecting reinforced concrete.

The corrosion-inhibiting effect of the 'alkoxy corrosion inhibitors' could be demonstrated with the aid of electrochemical measurements. It is possible to show that a significant increase in the polarization resistance can be achieved with 'alkoxy corrosion inhibitors' but that, in contrast to known corrosion inhibitors, such as, for example, nitrites, vanadates and molybdates, they show only a small increase ($\Delta E$) of the rest potential in comparison with the zero sample, so that the danger of macroelement formation is reduced. 'Alkoxy corrosion inhibitors' are therefore substantially superior to the corrosion inhibitors mentioned, not only with regard to their diffusability in concrete but also because of their better corrosion inhibition effect.

The hydraulically setting composition according to the invention can be used in different ways.

Firstly, steel-containing structures can be produced by means of the composition. For this purpose, the composition is mixed with water. The steel is then covered or enveloped with this material and hardening is effected. The erection of reinforced concrete structures, in particular of buildings, tunnels and bridges, is a particularly preferred example of this.

Secondly, the hydraulically setting composition according to the invention may be a mortar, in particular polymer-modified repair mortars, synthetic resin-modified mortars or a sludge comprising hydraulically setting material and water, to which the 'alkoxy corrosion inhibitor' has been added. Here, this composition is applied to exposed reinforcing steel after mixing with water. As mentioned below, the reinforcing steel may already have been treated beforehand with a surface-modifying agent according to the invention. The mortar mixed with water coats or envelopes the reinforcing steel. After application of a mortar containing the 'alkoxy corrosion inhibitor', said mortar hardens. This application represents a renovation method for hardened concrete, in particular old concrete. It is used especially in cases of advanced corrosion of the reinforcing steel (where the cross-sectional loss is too great, this should be replaced by new reinforcing steel) and chipping of concrete in the presence of relatively high chloride concentrations in the concrete layer covering the steel reinforcement.

The hydraulically setting composition is usually stored as a powder in the absence of moisture and comes into contact with water immediately before use. The amount of water used is very important for the final properties of the hardened composition. In the case of cement, the person skilled in the art uses the so-called water/cement ratio for this purpose. The mixing with water is effected manually or advantageously mechanically. Depending on the type of components of the composition, the composition mixed with water has different characteristics. For example, any intermediate stages of consistency can be realized, from brushable cement slurries through pumpable concretes to stable repair mortars. The compositions have no substantial mechanical strengths immediately after mixing with water. However, the systems harden by hydraulic setting to give high-strength materials.

The surface-modifying agent according to the invention can be used in different ways. Firstly, the surface-modifying agent can be applied to the steel surface. After the surface modification, the steel treated in this manner is covered or enveloped with a hydraulically setting composition after mixing of said composition with water.

In an embodiment of the invention, the surface-modifying agent is applied to reinforcing steel after production of the steel, with the result that the reinforcing steel is protected at least temporarily from corrosion during storage and transport, before it is combined with fresh concrete and hardens with formation of a reinforced steel structure.

Secondly, the surface-modifying agent for structural steel can be applied to the surface of already hardened reinforced concrete, in particular old concrete. The surface-modifying agent for structural steel, or at least the components contained therein which have corrosion inhibition activity, penetrates or penetrate into the concrete and finally reach the reinforcing steel. Such a use is a method for renovating reinforced concrete.

A further possibility of using the surface-modifying agent for structural steel is the application thereof to exposed reinforcing steel. The reinforcing steel treated in this manner can then be coated with a customary repair mortar or customary concrete, or it can be coated with a hydraulically setting composition according to the invention.

The application of the surface-modifying agent for structural steel can be effected in various ways, for example by coating, spraying, in particular airless spraying, immersion, flooding, pouring or application by means of a brush, paint roller, cloth or sponge. The application is advantageously repeated several times in succession. The penetration of the surface-modifying agent or of the 'alkoxy corrosion inhibitor' from the surface of the concrete to the structural steel can, as already described, be enhanced by additives present in the formulation. On the other hand, the moisture in the concrete plays an important role. Dry concrete sucks up the surface-modifying agent very much more strongly than moisture-saturated concrete. Furthermore, it may be advantageous to keep the concrete surfaces moist with water after the final application, in order to promote the penetration by means of water absorbed by capillary forces.

The advantageous effect of the hydraulically setting composition according to the invention and of the surface-modifying agent is explained by the fact that the diesters introduced into the concrete slowly hydrolyze with the alkalis present in the concrete to give monoester salts. These have a better corrosion-inhibiting effect than the diesters themselves. The processes according to the invention have the major advantage that it is also possible to use those compounds in which the calcium salts of the monoester salts are sparingly soluble and hence diffuse more slowly than the diesters. The monoester having the better corrosion inhibition effect is so to speak masked as a diester and penetrates into the concrete. Only in the interior of the concrete is the corrosion-inhibiting compound having better activity gradually released by hydrolysis.

EXAMPLES

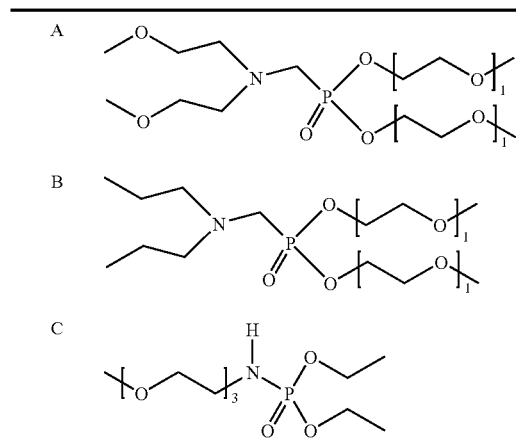

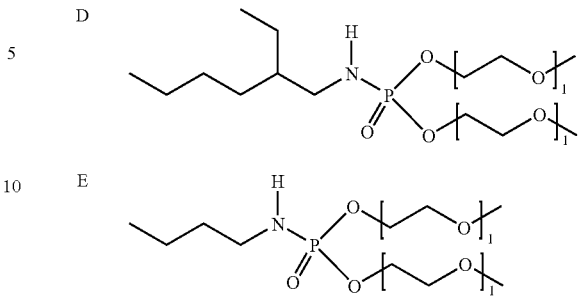

| Ref. 1. | Aminotrismethylenephosphonic acid (Dequest 2000, Monsanto) (50% aq) |
| Ref. 2. | 2-Phosphonobutane-1,2,4-tricarboxylic acid (Bayhibit AM (Bayer) (50% aq) |
| Ref. 3. | Calcium nitrite |
| Ref. 4. | Monoethanolamine |

The preparation of the corrosion inhibitors A, B, C, D and E is effected as follows:

Example 1

Transesterification of diethyl phosphite to di(methylpolyethyleneglycoxy)phosphite

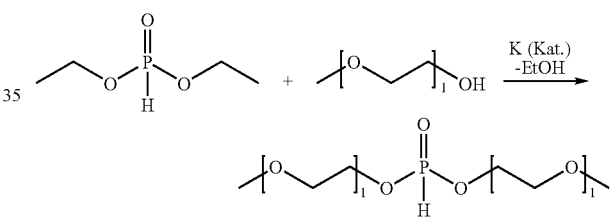

Diethyl phosphite (12.8 g, 0.093 mol) and Pluriol® A275E (50 g, 0.186 mol, available from BASF AG) were initially introduced together into a 500 ml flask. After the addition of potassium (20 mg, 0.5 mmol) as a catalyst, the reaction was heated to 170° C. and EtOH (3.4 g) were distilled off at atmospheric pressure. The remaining EtOH was evaporated at 20 mmHg. The yield was 95-98%.

Example 2

Preparation of 2-[2-(2-methoxyethoxy)ethoxy]ethylamines 200 g of triethylene glycol monomethyl ether (Fluka) was initially introduced with a catalyst and 700 ml of THF and into a 2.5 l stirred autoclave. Blanketing with nitrogen was then carried out, after which 500 ml of ammonia were added at room temperature. Thereafter, hydrogen was added at room temperature and heating to 200° C. was effected with stirring. On reaching 200° C., the pressure was increased by further addition of hydrogen. Thereafter, stirring was effected for 12 hours at 200° C. and cooling to room temperature was carried out. After filtration, addition of silica gel and further filtration, the clear colorless solution was evaporated down under a rotary evaporator. The amine was used without further purification.

Preparation of A and B

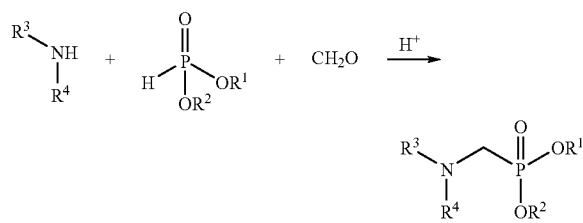

The di(methylpolyethyleneglycoxy)phosphite from example 1 (0.1 mol) was added dropwise in 1 hour to a mixture of the respective amine (0.1 mol), formaldehyde (36.5% strength solution, 0.1 mol) and o-phosphoric acid (85% strength, 5% by weight) with cooling to ~11° C. Thereafter, the reaction mixture was heated to 90° C. and kept at this temperature for 3 h.

Preparation of C, D and E

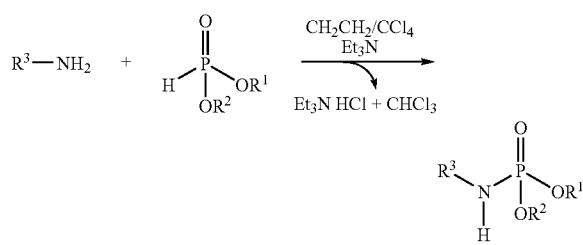

The di(methylpolyethyleneglycoxy)phosphite from example 1 (0.092 mol), or diethyl phosphite (0.092 mol) in the case of the preparation of C, were dissolved in a 1:1 $CCl_4/CH_2Cl_2$ mixture (185 ml), and the respective amine (example 2 or commercially available) (0.092 mol) was added. Finally, triethylamine (0.092 mol) was added dropwise. The white triethylammonium hydrochloride powder was filtered and the solvent was distilled off. The desired substances were obtained as transparent liquid in a yield of about 76%.

Composition 'Test Mortar 0-3 mm':
880 g of CEM I 42.5
320 g of limestone filler
180 g of quartz sand fraction 0.08-0.2 mm
280 g of quartz sand fraction 0.1-0.5 mm
370 g of quartz sand fraction 0.3-0.8 mm
440 g of quartz sand fraction 0.8-1.2 mm
630 g of quartz sand fraction 1.5-2.0 mm
800 g of quartz sand fraction 2.0-3.0 mm
Composition 'Test Concrete 0-32 mm':
7.50 kg of CEM I 42.5 (corresponding to 300 kg of cement per $m^3$ of concrete)
2.50 kg of limestone filler
17.50 kg of river sand 0-4 mm
7.50 kg of river sand 4-8 mm
7.50 kg of river sand 8-16 mm
15.00 kg of river sand 16-32 mm
Composition 'Test Concrete 0-16 mm':
11.25 kg of CEM I 42.5 (corresponding to 300 kg of cement per $m^3$ of concrete)
0.75 kg of limestone filler
39.00 kg of river sand 0-4 mm
11.25 kg of river sand 4-8 mm
24.00 kg of river sand 8-16 mm Test Methods The mortars and concretes were mixed according to EN 480-1. The determination of the characteristics in the mortar (slump, air void content, strengths) were carried out according to DIN 18555, and the determination of the concrete data in agreement with DIN 1048.

Comparison 1: Fresh Mortar Properties and Development of the Strength of Mortar on Addition of Various Corrosion Inhibitors:

Test Conditions:

CEM I 42.5
Test mortar mix 0-3 mm
Water/cement ratio: 0.545
Processing temperature 20° C.
Metering data in percent by mass of corrosion inhibitor, based on cement mass
Aftertreament of the mortar: Storage in a conditioned room at 20° C. and 95% relative humidity.

The test results from table 1 show that the comparative corrosion inhibitors Ref. 1. and Ref. 2., in contrast to the 'alkoxy corrosion inhibitors' A and B, particularly at relatively high inhibitor concentrations, with identical water/cement ratios, very adversely affect the early compressive strength values as well as the slump of mortar.

TABLE 1

Comparison of fresh mortar properties and development of strength of mortar - influence of the inhibitor and inhibitor concentrations

| Corrosion inhibitor | | Slump [mm] | | Air content [%] | | Compressive strength [MPa] | |
|---|---|---|---|---|---|---|---|
| | Dose [% by wt.] | 3 min | 30 min | 3 min | 30 min | 1 day | 7 days |
| None | 0.00 | 183 | 173 | 4.6 | 4.9 | 13.8 | 48.4 |
| A | 1.00 | 184 | 172 | 5.4 | 5.8 | 12.9 | 46.7 |
| B | 1.00 | 187 | 179 | 5.4 | 5.8 | 12.4 | 44.5 |
| Ref. 1. | 0.10 | 207 | 170 | 4.0 | 4.0 | 2.2 | n.d.** |
| Ref. 1. | 0.20 | 232 | 188 | 3.2 | 4.2 | <0.1* | n.d.** |
| Ref. 1. | 0.50 | 230 | 213 | 3.9 | 5.0 | <0.1* | 0.4 |
| Ref. 2. | 0.10 | 212 | 187 | 3.6 | 4.0 | <0.1* | n.d.** |
| Ref. 2. | 0.20 | 226 | 192 | 4.0 | 4.9 | <0.1* | n.d.** |
| Ref. 2. | 0.50 | 222 | 213 | 3.8 | 4.4 | <0.1* | 0.5 |

* Mortar samples still soft at time of testing (compressive strength values <0.1 MPa).
**n.d.= not determined.

Comparison 2: Fresh Mortar Properties and Development of Strength of Mortar on Addition of Various Corrosion Inhibitors and Flow Improvers:

Test Conditions:

Test mortar mix 0-3 mm
Water/cement: 0.430
Processing temperature 20° C.
Addition of 1.00% of a flow improver based on sulfonated naphthalene/formaldehyde condensates
Addition in the case of D and E of 0.3% by weight of antifoam, based on the mass of corrosion inhibitor, consisting of 1 part by mass of tributyl phosphate and 2 parts by mass of a mineral oil-based antifoam
Metering data in percent by mass of corrosion inhibitor, based on cement mass Aftertreatment of the mortar: Storage in a conditioned room at 20° C. and 95% relative humidity.

TABLE 2

Comparison of fresh mortar properties and development of strength of mortar on addition of flow improver - influence of the inhibitor and inhibitor concentrations.

| Corrosion inhibitor | | Slump | | Air content | | Compressive strength [MPa] | | |
|---|---|---|---|---|---|---|---|---|
| | Dose | [mm] | | [%] | | | | |
| | [% by wt.] | 3 min | 30 min | 3 min | 30 min | 1 day | 3 days | 28 days |
| None | 0.00 | 188 | 157 | 4.3 | 4.5 | 33.1 | 61.0 | 67.7 |
| A | 0.50 | 183 | 157 | 5.3 | 5.7 | 32.1 | 58.9 | 66.9 |
| B | 0.50 | 176 | 155 | 5.4 | 5.6 | 30.7 | 57.3 | 66.2 |
| C | 0.50 | 192 | 160 | 4.2 | 4.6 | 29.6 | 55.6 | 64.5 |
| D | 0.50 | 184 | 157 | 4.5 | 5.0 | 30.7 | 57.4 | 65.4 |
| E | 0.50 | 193 | 154 | 4.7 | 6.2 | 29.3 | 56.7 | 65.0 |
| A | 1.00 | 180 | 154 | 5.6 | 6.0 | 30.2 | 57.4 | 65.3 |
| B | 1.00 | 175 | 149 | 5.3 | 5.8 | 28.7 | 56.5 | 64.1 |
| C | 1.00 | 194 | 162 | 4.8 | 5.2 | 27.9 | 54.4 | 63.8 |
| D | 1.00 | 192 | 154 | 4.7 | 5.1 | 28.1 | 56.4 | 64.1 |
| E | 1.00 | 183 | 153 | 5.0 | 5.5 | 28.6 | 56.1 | 62.5 |

The results from table 2 for test mortars modified with flow improvers show that the test mortars containing 'alkoxy corrosion inhibitors' A, B, C, D and E have no marked deteriorations with respect to processing properties or compressive strengths in comparison with the test mortar without corrosion inhibitors, even at relatively high concentrations.

Comparison 3: Fresh Mortar Properties and Development of Strength of Mortar on Addition of Corrosion Inhibitors Combined with Air-entraining Agents:

Test Conditions:

Test mortar mix 0-3 mm
Water/cement: 0.545
Processing temperature 20° C.
Metering data in percent by mass of corrosion inhibitor or air-entraining agent, based on cement mass
Aftertreatment of the mortar: Storage in a conditioned room at 20° C. and 95% relative humidity
Addition of an air-entraining agent based on natural root resins On the basis of the results of the corrosion inhibitors A and B in comparison with the sample without 'alkoxy corrosion inhibitors', table 3 shows that 'alkoxy corrosion inhibitors' do not adversely influence the effect of the air-entraining agents.

Comparison 4: Fresh Mortar Properties of Mortar on Addition of Various Corrosion Inhibitors and Air-entraining Agents and Flow Improvers:

Test Conditions:
Test mortar mix 0-3 mm
Water/cement: 0.430
Processing temperature 20° C.
Addition of 1.00% of a flow improver based on sulfonated naphthalene/formaldehyde condensates
Addition of an air-entraining agent based on natural root resins
Addition in the case of D and E of 0.3% by weight of antifoam, based on the mass of corrosion inhibitor, consisting of 1 part by mass of tributyl phosphate and 2 parts by mass of a mineral oil-based antifoam.
Metering data in percent by mass of corrosion inhibitor or air-entraining agent, based on cement mass
Aftertreatment of the mortar: Storage in a conditioned room at 20° C. and 95% relative humidity.

TABLE 4

Comparison of fresh mortar properties on addition of flow improver and air entraining agent.

| Corrosion inhibitor | Air-entraining agent | Slump | | Air content | |
|---|---|---|---|---|---|
| Dose | Dose | [mm] | | [%] | |
| [% by wt.] | [% by wt.] | 3 min | 30 min | 3 min | 30 min |
| None | 0.00 | 0.40 | 190 | 160 | 7.5 | 7.0 |
| D | 0.50 | 0.40 | 204 | 170 | 7.8 | 8.1 |
| D | 0.50 | 0.60 | 200 | 185 | 8.9 | 9.3 |
| D | 0.50 | 0.70 | 210 | 198 | 10.5 | 11.5 |
| E | 0.50 | 0.40 | 203 | 168 | 7.2 | 7.3 |
| E | 0.50 | 0.60 | 209 | 171 | 9.1 | 9.2 |
| E | 0.50 | 0.70 | 216 | 190 | 10.2 | 11.0 |

TABLE 3

Comparison of fresh mortar properties on addition of air-entraining agents

| Corrosion inhibitor | Air-entraining agent | Slump | | Air content | | Compressive strength [MPa] | | |
|---|---|---|---|---|---|---|---|---|
| Dose | Dose | [mm] | | [%] | | | | |
| [% by wt.] | [% by wt.] | 3 min | 30 min | 3 min | 30 min | 1 day | 7 days | 28 days |
| None | 0.00 | 0.00 | 182 | 178 | 4.7 | 4.9 | 15.1 | 44.0 | 51.7 |
| A | 0.50 | 0.00 | 188 | 187 | 5.8 | 5.8 | 12.8 | 39.7 | 49.8 |
| B | 0.50 | 0.00 | 190 | 180 | 5.7 | 5.8 | 12.8 | 40.5 | 49.3 |
| A | 1.00 | 0.00 | 185 | 188 | 5.4 | 5.9 | 12.5 | 40.3 | 47.8 |
| B | 1.00 | 0.00 | 187 | 185 | 5.6 | 5.8 | 12.5 | 41.1 | 49.3 |
| None | 0.00 | 0.20 | 190 | 195 | 13.0 | 13.4 | 10.6 | 31.9 | 36.5 |
| A | 0.50 | 0.20 | 193 | 190 | 14.0 | 13.8 | 9.7 | 29.7 | 36.5 |
| B | 0.50 | 0.20 | 196 | 197 | 14.5 | 13.6 | 9.4 | 28.8 | 36.2 |
| A | 1.00 | 0.20 | 193 | 189 | 14.2 | 13.5 | 8.7 | 28.1 | 34.5 |
| B | 1.00 | 0.20 | 197 | 194 | 14.7 | 14.4 | 8.4 | 27.7 | 33.8 |

The results from table 4 for test mortars modified with flow improvers and air-entraining agents show that the test mortars containing 'alkoxy corrosion inhibitors' D and E have no marked deteriorations with respect to processing properties in comparison with the test mortar without corrosion inhibitors, even at relatively high concentrations of air-entraining agent.

Comparison 5: Fresh Concrete Properties and Development of Strength of Concrete on Addition of Various Corrosion Inhibitors:

Test Conditions:

Test concrete mix 0-32 mm

Water/cement: 0.540

Processing temperature 20° C.

Metering data in percent by mass of corrosion inhibitor, based on cement mass

Aftertreatment of the concrete: Storage in a conditioned room at 20° C. and 95% relative humidity Compressive strength test on cubes with edge length of 120 mm.

TABLE 5

Comparison of fresh concrete properties

| Corrosion inhibitor | | Slump | Air content | Compressive strength [MPa] | | | |
|---|---|---|---|---|---|---|---|
| Dose | | [cm] | [%] | 1 | 3 | 7 | 28 |
| [% by wt.] | 3 min | 30 min | 3 min | day | days | days | days |
| None | 0.00 | 42 | 35 | 1.5 | 18.3 | 32.5 | |
| A | 0.50 | 43 | 35 | 1.8 | 17.1 | 31.4 | |
| A | 1.00 | 42 | 34 | 2.0 | 16.2 | 28.7 | |
| B | 0.50 | 44 | 36 | 2.1 | 16.7 | 30.3 | |
| B | 1.00 | 43 | 37 | 2.0 | 15.9 | 27.9 | |

The results from table 5 show that with test concretes containing 'alkoxy corrosion inhibitors' A and B no significant differences can be found in comparison with the test concrete without corrosion inhibitors, either in the processibility of the concrete or in the air content.

Comparison 6: Electrochemical Measurements: Comparison of Different Corrosion Inhibitors:

The linear polarization resistance of solutions of corrosion inhibitors in contact with structural steel ST-37 was measured by means of the potentiostat-galvanostat Versastat II from Perkin-Elmer. The reference electrode used was Ag/AgCl (3 M KCl solution, E=197 mV). A platinum net or platinum spiral having an area of 3 cm$^2$ and a distance of 8-12 cm from the working electrode served as the opposite electrode (arrangement parallel to the working electrode). The test sheet to be investigated served as the working electrode. The test sheet (2×5 cm$^2$, steel 1.0037) was subjected to the following pretreatment (A) cathodic alkaline degreasing (B) immersion in water (C) cathodic derusting in 10% of diammonium citrate (D) immersion in water A circular area of 1 cm$^2$ of the test sheet in contact with the test electrolyte consisting of 0.5 percent by mass of the respective corrosion inhibitor in 0.03 molar sodium chloride solution was present in the measuring cell.

The linear polarization was measured in the range of 20 mV about the rest potential at a measuring rate of 0.166 mV/s.

TABLE 6

Electrochemical measurements

| Corrosion inhibitor | Rest potential [mV] | Polarization resistance [kΩ] |
|---|---|---|
| None | −584 to −540 | 1 to 2 |
| C | −453 to −443 | 3 to 4 |
| D | −328 to −340 | 3 to 4 |
| E | −333 to −349 | 4 to 6 |
| Ref. 3. | −3 to −27 | 5 to 7 |

The measured values of the electrochemical measurements in table 6 show that, although calcium nitrite (Ref. 3.) as a known corrosion inhibitor for structural steel acts substantially the effect as a corrosion inhibitor from the increase of the polarization resistance and from the increase of the rest potential, a very sharp increase (ΔE) of the rest potential in comparison to the zero sample of more than 500 mV takes place, which is known to be a major disadvantage of the known corrosion inhibitors. This can in fact lead to the formation of macroelements. In the case of the 'alkoxy corrosion inhibitors' C, D and E, a significant increase in the polarization resistance is likewise achieved, and hence a substantial effect as a corrosion inhibitor is shown, and at the same time the rest potential increases only by 100 to 200 mV. In the case of such small potential differences, the danger of macroelement formation is substantially reduced. By means of these measurements, it is therefore possible to show that 'alkoxy corrosion inhibitors' is superior to the known corrosion inhibitors.

Comparison 7: Penetration of Surface-applied Corrosion Inhibitors in Hardened Concrete Samples:

In order to test the penetration behavior of the 'alkoxy corrosion inhibitors', small concrete panels 75 mm long, 20 mm wide and 4 mm thick were used. The small concrete panels were placed—similarly to thin-layer chromatography—perpendicularly in a test solution comprising in each case 10% by weight of the corrosion inhibitors in water, so that they dipped into the solution by about 1 cm at the bottom edge. In order to prevent evaporation of the test solution, the tests were carried out in a closed vessel, for example a small glass container of a suitable size having a snap-on lid. After one day, the test solution has migrated upward to the top edge of the small panel. For analysis, a sample was broken off after one day from the upper third of the small concrete panel and ground, and the phosphorus content was analyzed.

The hydrolysis product of the corrosion inhibitor (hydrolysis product A) was prepared as follows: 50.0 g of tap water and 5.4 g of sodium hydroxide were added to 50.0 g of the corrosion inhibitor A with stirring. The resulting solution was stirred gently at room temperature for 2 days. The solids content of the solution was then adjusted to 10% by mass by adding further tap water.

TABLE 7

Penetration behavior

| Corrosion inhibitor | P content [mg/100 g] |
|---|---|
| None | 21 |
| A | 55 |
| Hydrolysis product A | 52 |
| B | 40 |
| D | 46 |
| E | 38 |

The results of table 7 show that the corrosion inhibitors penetrate to a considerable extent into the concrete, which is evident from the significantly higher phosphorus concentrations in comparison with the zero samples.

The invention claimed is:

1. A hydraulically setting composition, characterized in that it contains esters or ester salts, comprising alkoxy groups, of phosphorus-oxygen acids of the general formula (I), (II), (III) or (IV)

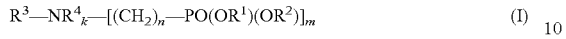
$$R^3—NR^4_k—[(CH_2)_n—PO(OR^1)(OR^2)]_m \quad (I)$$

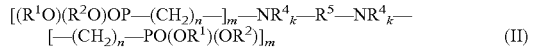
$$[(R^1O)(R^2O)OP—(CH_2)_n—]_m—NR^4_k—R^5—NR^4_k—[—(CH_2)_n—PO(OR^1)(OR^2)]_m \quad (II)$$

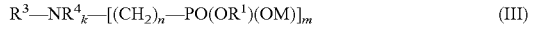
$$R^3—NR^4_k—[(CH_2)_n—PO(OR^1)(OM)]_m \quad (III)$$

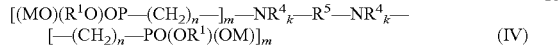
$$[(MO)(R^1O)OP—(CH_2)_n—]_m—NR^4_k—R^5—NR^4_k—[—(CH_2)_n—PO(OR^1)(OM)]_m \quad (IV)$$

where
n is an integer from 0 to 10,
m+k is 2 and m is 1 or 2 and k is 0 or 1,
at least one of the radicals $R^1$, $R^2$ and optionally $R^3$ is an alkoxy group of the general formula —[$CH_2$—$CHR^6$—O]$_1R^7$, where 1 is from 2 to 30 and $R^6$ and $R^7$ are each H or $CH_3$,
and the radicals $R^1$ and $R^2$, where they are not alkoxy groups, are straight-chain or branched, optionally substituted $C_1$- to $C_6$-alkyl groups,
and $R^3$, where it is not an alkoxy group, is a straight-chain or branched, optionally substituted, $C_1$- to $C_{20}$-alkyl group or aryl group,
$R^4$ is H or a straight-chain or branched, optionally substituted $C_1$- to $C_6$-alkyl group,
$R^5$ is a divalent, bridging group, and
M is at least one cation selected from the group consisting of alkali metal, alkaline earth metal or ammonium ions.

2. The hydraulically setting composition as claimed in claim 1, characterized in that n is 0 or 1.

3. The hydraulically setting composition as claimed in claim 1, characterized in that k is 1 and m is 1.

4. The hydraulically setting composition as claimed in claim 1, characterized in that 1 has a value of from 3 to 20.

5. The hydraulically setting composition as claimed in claim 1, characterized in that $R^6$ is H.

6. The hydraulically setting composition as claimed in claim 1, characterized in that $R^7$ is H.

7. The hydraulically setting composition as claimed in claim 1, characterized in that it additionally contains at least one further corrosion inhibitor selected from the group consisting of monoethanolamine, diethanolamine, triethanolamine, N-methylethanolamine, N,N-dimethylethanolarnine, N-ethylethanolamine, N,N-diethylethanolamine, N-methyldiethanolamine, 2-hydroxyethylethylenediamine and saltsof organic acids thereof.

8. A surface-modifying agent for structural steel, characterized in that it contains or consists of esters or ester salts, comprising alkoxy groups, of phosphorus-oxygen acids of the general formula (I), (II), (III) or (IV):

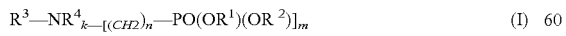
$$R^3—NR^4_k—[(CH_2)_n—PO(OR^1)(OR^2)]_m \quad (I)$$

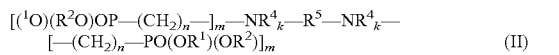
$$[(^1O)(R^2O)OP—(CH_2)_n—]_m—NR^4_k—R^5—NR^4_k—[—(CH_2)_n—PO(OR^1)(OR^2)]_m \quad (II)$$

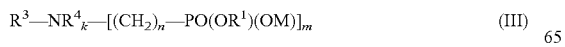
$$R^3—NR^4_k—[(CH_2)_n—PO(OR^1)(OM)]_m \quad (III)$$

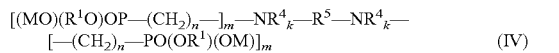
$$[(MO)(R^1O)OP—(CH_2)_n—]_m—NR^4_k—R^5—NR^4_k—[—(CH_2)_n—PO(OR^1)(OM)]_m \quad (IV)$$

where
n is an integer from 0 to 10,
m+k is 2 and m is 1 or 2 and k is 0 or 1,
at least one of the radicals $R^1$, $R^2$ and optionally $R^3$ is an alkoxy group of the general formula —[$CH_2$—$CHR^6$—O]$_1R^7$, where 1 is from 2 to 30 and $R^6$ and $R^7$ are each H or $CH_3$,
and the radicals $R^1$ and $R^2$, where they are not alkoxy groups, are straight-chain or branched, optionally substituted $C_1$- to $C_6$-alkyl groups,
and $R^3$, where it is not an alkoxy group, is a straight-chain or branched, optionally substituted, $C_1$- to $C_{20}$-alkyl group or aryl group,
$R^4$ is H or a straight-chain or branched, optionally substituted $C_1$- to $C_6$-alkyl group,
$R^5$ is a divalent, bridging group, and
M is at least one cation selected from the group consisting of alkali metal, alkaline earth metal or ammonium ions.

9. The surface-modifying agent for structural steel as claimed in claim 8, characterized in that n is 0 or 1.

10. The surface-modifying agent for structural steel as claimed in claim 8, characterized in that k is 1 and m is 1.

11. The surface-modifying agent for structural steel as claimed in claim 8, characterized in that l has a value of from 3 to 20.

12. The surface-modifying agent for structural steel as claimed in claim 8, characterized in that $R^6$ is H.

13. The surface-modifying agent for structural steel as claimed in claim 8, characterized in that $R^7$ is H.

14. The surface-modifying agent for structural steel as claimed in claim 8, characterized in that it additionally contains at least one further corrosion inhibitor selected from the group consisting of monoethanolamine, diethanolamine, triethanolamine, N-methylethanolamine, N,N-dimethylethanolamine, N-ethylethanolamine, N,N-diethylethanolamine, N-methyldiethanolamine, 2-hydroxyethylethylenediamine and salts of organic acids thereof.

15. A process for the production of steel-containing structures, characterized in that a hydraulically setting composition as claimed in claim 1 is mixed with water and the steel is covered or enveloped therewith and hardened.

16. A process for the production of steel-containing structures, characterized in that a surface-modifying agent as claimed in claim 8 is applied to the steel surface and the surface-modified steel is then covered or enveloped with a hydraulically setting composition after mixing thereof with water.

17. A process for renovating reinforced concrete, characterized in that a surface-modifying agent as claimed in claim 8 is applied to the concrete surface.

18. A process for renovating reinforced concrete, characterized in that a surface-modifying agent as claimed in claim 8 is applied to exposed reinforcing steel and then covered again with a repair mortar or concrete.

19. A process for renovating reinforced concrete, characterized in that a hydraulically setting composition as claimed in claim 1 is applied to exposed reinforcing steel.

20. A process for the preparation of a hydraulically setting composition as claimed in claim 1, characterized in that esters or ester salts, comprising alkoxy groups, of phosphorus oxygen acids is added to the dry binder,mortar or concrete or to the binder, mortar or concrete mixed with water, in the factory, on the building site, in the mixer or in the delivery pump, or is added directly to the mix via a staticmixer having a powder metering device or liquid metering device.

* * * * *